United States Patent
Soo et al.

(10) Patent No.: US 8,801,791 B2
(45) Date of Patent: Aug. 12, 2014

(54) SPINAL INTERBODY SPACER

(75) Inventors: Teck Soo, Franklin, MI (US); Peter Bono, Franklin, MI (US); Todd Wallenstein, Ashburn, VA (US); Peter Harris, Leesburg, VA (US)

(73) Assignees: K2M, Inc., Leesburg, VA (US); Teck Soo, Franklin, MI (US); Peter Bono, Franklin, MI (US)

( * ) Notice: Subject to any disclaimer, the term of this patent is extended or adjusted under 35 U.S.C. 154(b) by 1406 days.

(21) Appl. No.: 11/904,569

(22) Filed: Sep. 27, 2007

(65) Prior Publication Data
US 2008/0288076 A1 Nov. 20, 2008

Related U.S. Application Data

(60) Provisional application No. 60/847,595, filed on Sep. 27, 2006.

(51) Int. Cl.
*A61F 2/44* (2006.01)

(52) U.S. Cl.
USPC ................... 623/17.16; 623/17.11

(58) Field of Classification Search
USPC .......................... 623/17.11–17.16
See application file for complete search history.

(56) References Cited

U.S. PATENT DOCUMENTS

| | | | |
|---|---|---|---|
| 4,834,757 A | 5/1989 | Brantigan | |
| 5,192,327 A | 3/1993 | Brantigan | |
| 5,306,307 A * | 4/1994 | Senter et al. | 623/17.16 |
| 5,425,772 A | 6/1995 | Brantigan | |
| 5,443,514 A | 8/1995 | Steffee | |
| 5,554,191 A * | 9/1996 | Lahille et al. | 623/17.11 |
| 5,888,222 A * | 3/1999 | Coates et al. | 623/17.16 |
| 6,245,108 B1 | 6/2001 | Biscup | |
| 6,325,827 B1 | 12/2001 | Lin | |
| 6,447,544 B1 | 9/2002 | Michelson | |
| 6,447,547 B1 | 9/2002 | Michelson | |
| 6,478,823 B1 | 11/2002 | Michelson | |

(Continued)

FOREIGN PATENT DOCUMENTS

| | | |
|---|---|---|
| EP | 0 664 994 | 8/1995 |
| EP | 1 415 623 | 5/2004 |

(Continued)

OTHER PUBLICATIONS

International Search Report from European Application No. EP 07 01 9033 dated Jan. 22, 2008.

*Primary Examiner* — Eduardo C. Robert
*Assistant Examiner* — Lynnsy Schneider
(74) *Attorney, Agent, or Firm* — Carter, DeLuca, Farrell & Schmidt, LLP

(57) ABSTRACT

A spinal spacer for engagement between vertebrae includes a body having a substantially contoured first end surface at a distal end and a second end surface opposite thereto at a proximal end. The body extends between the first and second end surfaces to define top and bottom vertebral engaging surfaces that are opposed to one another. The body extends between the top and bottom vertebral engaging surfaces to define opposed side surfaces. The top and bottom vertebral engaging surfaces intersect with the side surfaces to provide a substantially quadrilateral cross-section with rounded corners. The top and bottom vertebral engaging surfaces have a substantially streamlined convex profile. The surfaces converge at the distal end to define a substantially atraumatic blunt nose having a tip configured with planar and/or convex surfaces.

18 Claims, 15 Drawing Sheets

(56) References Cited

U.S. PATENT DOCUMENTS

| | | | |
|---|---|---|---|
| 6,482,233 B1 | 11/2002 | Aebi et al. | |
| 6,676,703 B2 | 1/2004 | Biscup | |
| 6,719,794 B2 | 4/2004 | Gerber et al. | |
| 6,743,255 B2 | 6/2004 | Ferree | |
| 6,827,740 B1* | 12/2004 | Michelson | 623/17.11 |
| 6,890,355 B2 | 5/2005 | Michelson | |
| 6,942,698 B1 | 9/2005 | Jackson | |
| 6,991,654 B2 | 1/2006 | Foley | |
| 7,137,997 B2* | 11/2006 | Paul | 623/17.11 |
| 7,195,643 B2 | 3/2007 | Jackson | |
| 7,229,477 B2 | 6/2007 | Biscup | |
| 7,276,081 B1* | 10/2007 | Coates et al. | 623/17.11 |
| 7,311,734 B2 | 12/2007 | Van Hoeck et al. | |
| 2003/0114931 A1* | 6/2003 | Lee et al. | 623/17.11 |
| 2004/0117020 A1* | 6/2004 | Frey et al. | 623/17.11 |
| 2004/0127994 A1* | 7/2004 | Kast et al. | 623/17.16 |
| 2005/0027360 A1* | 2/2005 | Webb et al. | 623/17.11 |
| 2005/0149188 A1* | 7/2005 | Cook et al. | 623/17.11 |
| 2005/0288788 A1* | 12/2005 | Dougherty-Shah | 623/17.11 |
| 2006/0195190 A1* | 8/2006 | Lechmann et al. | 623/17.11 |
| 2007/0100452 A1* | 5/2007 | Prosser | 623/17.11 |
| 2008/0015695 A1* | 1/2008 | Eckman | 623/17.11 |
| 2008/0065219 A1* | 3/2008 | Dye | 623/17.16 |
| 2008/0077247 A1* | 3/2008 | Murillo et al. | 623/17.16 |
| 2008/0082173 A1* | 4/2008 | Delurio et al. | 623/17.16 |

FOREIGN PATENT DOCUMENTS

| | | |
|---|---|---|
| WO | WO 99/38461 | 8/1999 |
| WO | WO 04/000177 | 12/2003 |
| WO | WO 2006/042335 | 4/2006 |

* cited by examiner

SPINAL INTERBODY SPACER

CROSS-REFERENCE TO RELATED APPLICATIONS

This application claims priority to, and the benefit of, U.S. Provisional Patent Application No. 60/847,595, filed on Sep. 27, 2006, the entire contents of which are incorporated herein by reference in their entirety.

BACKGROUND

1. Technical Field

The present disclosure relates to devices for implantation between adjacent vertebrae. Specifically, the disclosure relates to a spinal interbody spacer that inhibits the collapse of the space between adjacent vertebrae after a discectomy.

2. Background of Related Art

After a partial or complete discectomy, the normally occupied space between adjacent vertebral bodies is subject to collapse and/or misalignment due to the absence of all or a part of the intervertebral disc. In such situations, the physician may insert one or more prosthetic spacers between the affected vertebrae to maintain normal disc spacing and/or the normal amount of lordosis in the affected region.

Typically, a prosthetic implant is inserted between the adjacent vertebrae and may include pathways that permit bone growth between the adjacent vertebrae until they are fused together. However, there exists a possibility that conventional prosthetic implants may be dislodged or moved from their desired implantation location due to movement by the patient before sufficient bone growth has occurred.

Therefore, a need exists for a spinal implant that provides a desired amount of lordosis, allows for bone growth between adjacent vertebrae, maintains the space between adjacent vertebrae during bone ingrowth, and resists dislocation from its implantation site.

SUMMARY

The present disclosure relates to a spinal interbody spacer for engagement between vertebrae. In one embodiment, the spacer includes a body having a substantially contoured first end surface at a distal end of the body and a second end surface opposite thereto at a proximal end of the body. The body extends between the first and second end surfaces to define top and bottom vertebral engaging surfaces. The top and bottom vertebral engaging surfaces are opposite to one another. The body extends between the top and bottom surfaces to define opposed side surfaces. The body is configured such that the top and bottom vertebral engaging surfaces intersect the side surfaces to provide a substantially quadrilateral cross-section with rounded corners. The body is configured such that the top and bottom vertebral engaging surfaces have a substantially streamlined convex profile, and the body is configured such that the convex top and bottom surfaces and the side surfaces converge at the distal end of the body to define a substantially atraumatic blunt nose having a tip with a linear portion between the converging side surfaces and a rounded shape between the top and bottom surfaces. The top and bottom vertebral engaging surfaces are convex and include first, second and third surface regions having distinct surface characteristics for insertion into the disc space and engagement with the vertebrae.

In another embodiment according to the present disclosure, the body is configured as described above except that the substantially convex top and bottom surfaces and the side surfaces converge at the distal end of the body to define a substantially atraumatic blunt nose with planar top and bottom surfaces and a rounded shape between the side surfaces. In yet a third embodiment, the atraumatic blunt nose may have curved top and bottom surfaces and planar side surfaces.

Furthermore, at least one of the top and bottom vertebral engaging surfaces may further include at least first and second surface regions having distinct surface characteristics. The surface characteristic of the first surface region may be such that the first surface region has a plurality of protrusions having a configuration and the surface characteristic of the second surface region may be such that the second surface region has a plurality of protrusions having a configuration, wherein the configuration of the plurality of protrusions of the second surface region differs from the configuration of the plurality of protrusions of the first surface region. The configuration of the plurality of protrusions of the second surface region may be such that the plurality of protrusions of the second surface region defines a set of pyramidal protrusions. Each of the plurality of pyramidal protrusions may have a position along the at least one of the top and bottom vertebral engaging surfaces having a substantially streamlined convex profile. Each of the plurality of pyramidal protrusions may define a first sloped face oriented towards the distal end of the body. In addition, each of the plurality of pyramidal protrusions may define a second face substantially orthogonal to the at least one of the top and bottom vertebral engaging surfaces at the respective position of the pyramidal protrusion, with the first sloped face and second face defining a bone engaging region therebetween. At least a portion of the bone engaging region extending between the first sloped and second of the pyramidal protrusions may be configured as a flat surface.

BRIEF DESCRIPTION OF THE DRAWINGS

Embodiments of the presently disclosed spinal interbody spacer are described herein with reference to the accompanying drawings, wherein.

DETAILED DESCRIPTION

Figure 1:
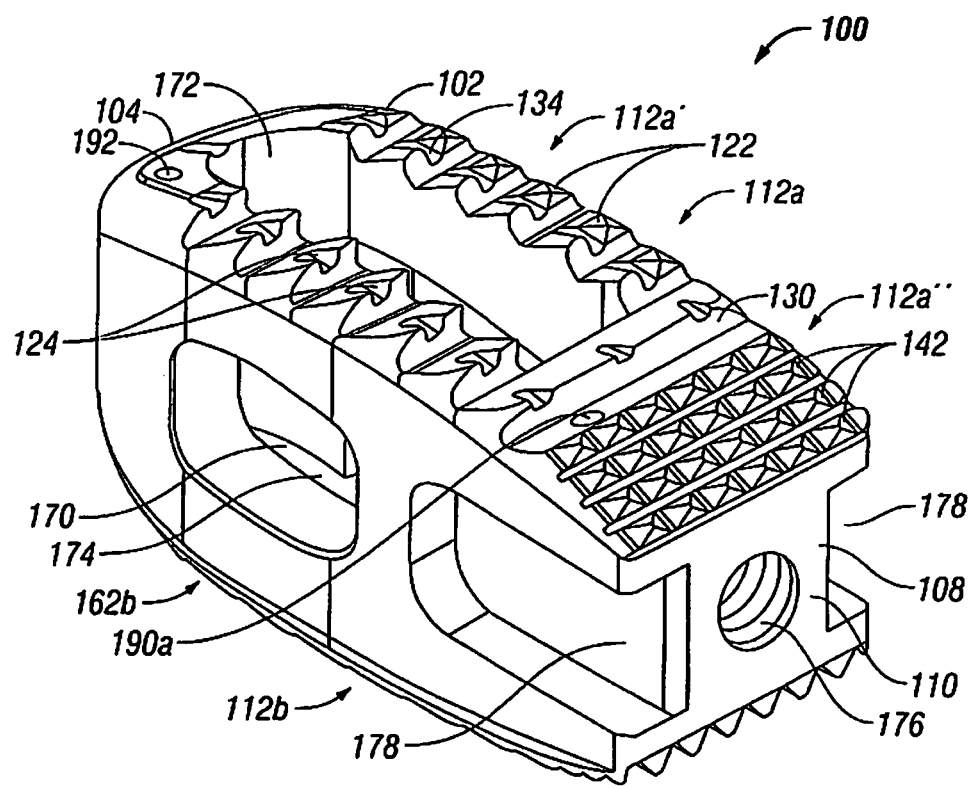
FIG. 1 is a perspective view generally from a trailing or proximal end of one embodiment of a spinal interbody spacer according to the present disclosure.

Embodiments of the presently disclosed spinal interbody spacer will now be described in detail with reference to the drawings, in which like reference numerals designate identical or corresponding elements in each of the several views.

In the drawings and in the description that follows, the term proximal refers to the portion of the device that is closest to the operator, while the term distal refers to the portion of the device that is furthest from the operator. Additionally, in the drawings and in the description that follows, terms such as front, rear, upper, lower, top, bottom, and the similar directional terms are used simply for convenience of description and are not intended to limit the disclosure attached hereto.

Referring now to FIGS. 1-12, there is disclosed one embodiment of a spinal interbody spacer 100 for engagement between vertebrae according to the present disclosure. More particularly, referring to FIGS. 1-6, in one embodiment, spinal interbody spacer 100 includes a body 102 having a substantially contoured first end surface 104 at a distal or leading end 106 of the body 102 and a second end surface 108 opposite thereto at a proximal or trailing end 110 of the body 102. The body 102 extends between the first and second end surfaces 104, 108, respectively, to define top and bottom vertebral engaging surfaces 112a, 112b, respectively. The top and bottom vertebral engaging surfaces 112a, 112b, respectively, are disposed opposite to one another. The body 102 also extends between the first and second end surfaces, 104, 108, respectively, to define opposed side surfaces 162a, 162b, respectively.

Figure 3:
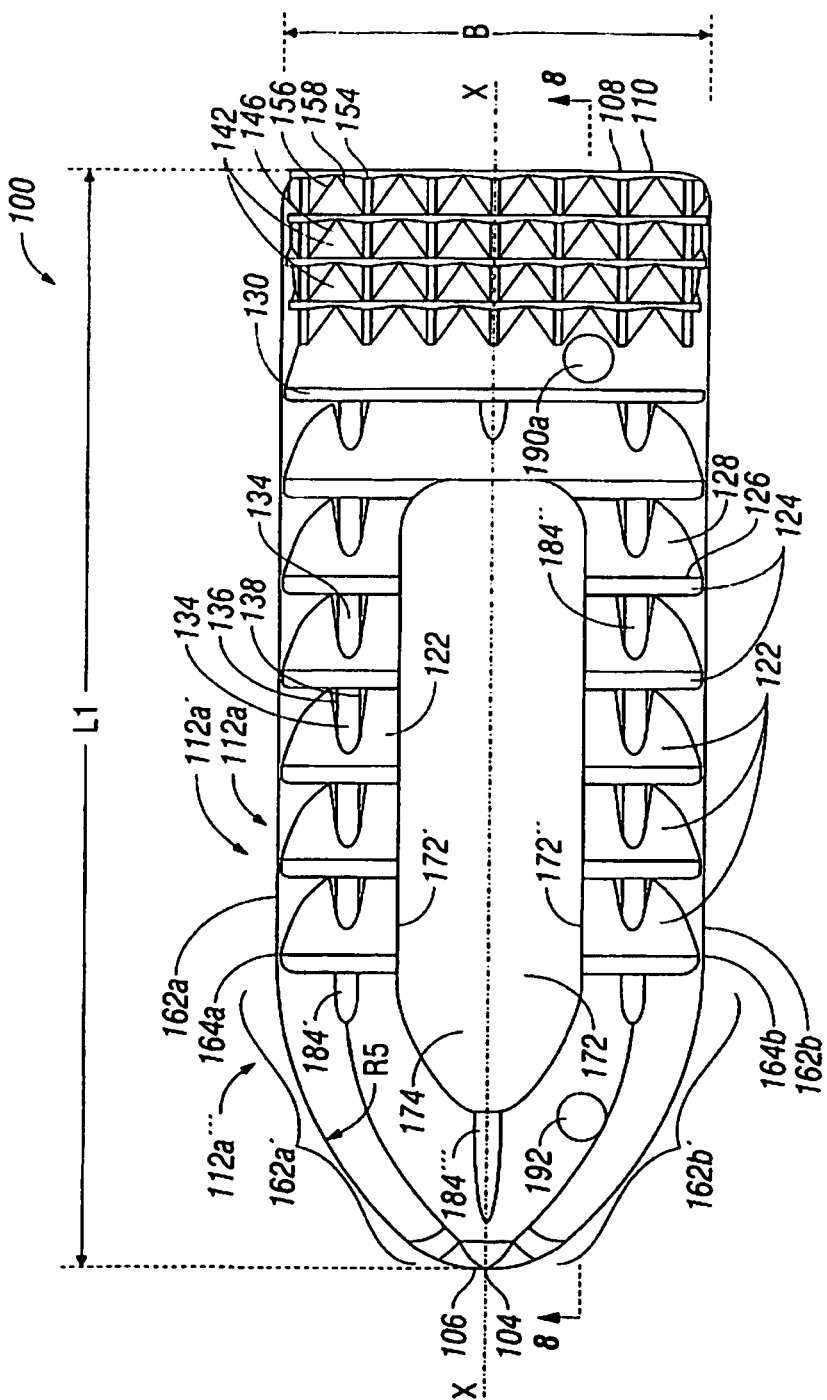
FIG. 3 is a top plan view of the spinal interbody spacer of FIG. 1 showing a vertebral-engaging surface.
Figure 4:
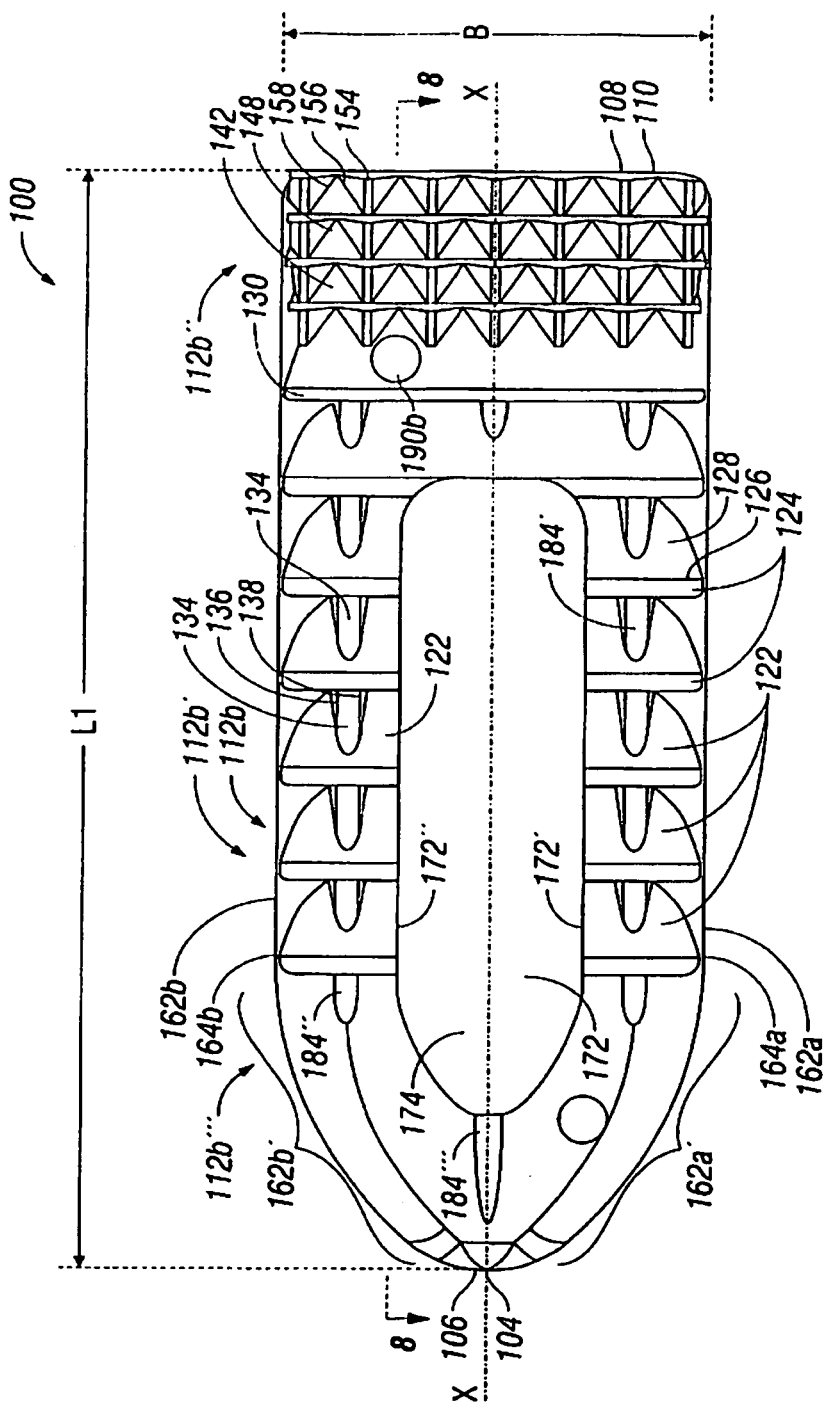
FIG. 4 is a bottom plan view of the spinal interbody spacer of FIG. 1 showing another vertebral-engaging surface.
Figure 5:
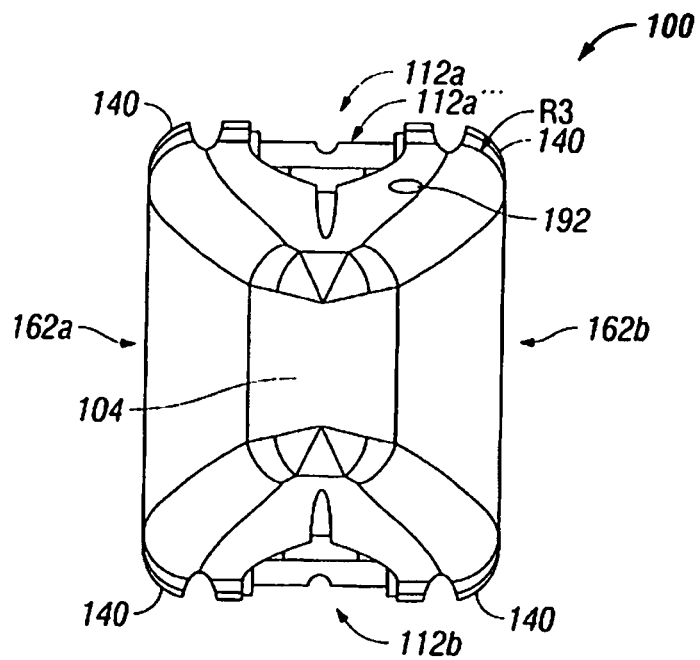
FIG. 5 is a front elevation view of the leading or distal end of the spinal interbody spacer.
Figure 6:
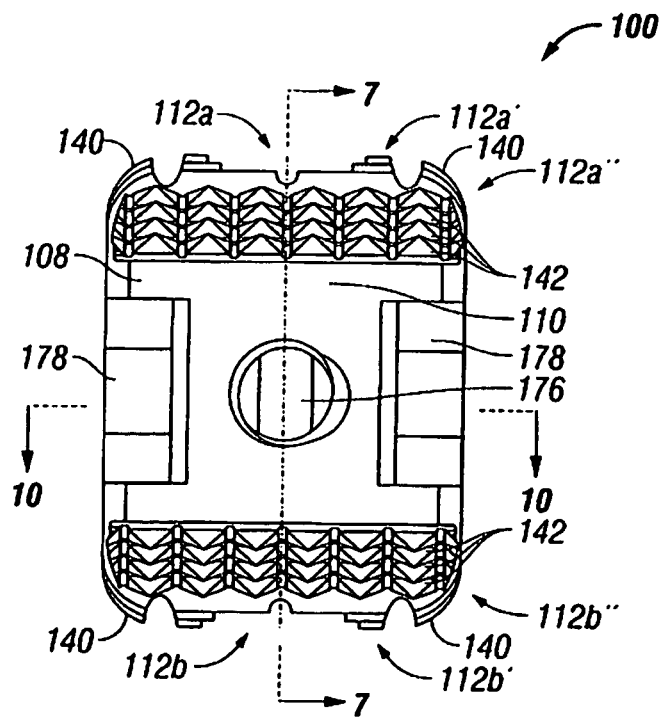
FIG. 6 is a rear elevation view of the trailing or proximal end of the spinal interbody spacer.

As best illustrated in FIGS. 5 and 6, the body 102 is configured such that the top and bottom vertebral engaging surfaces 112a, 112b intersect the side surfaces 162a, 162b, respectively, to provide a substantially quadrilateral cross-section with rounded corners 140. As illustrated in FIGS. 1-12, the body 102 has, by way of example, a substantially rectangular cross-section, although other quadrilateral shapes such as a square are also contemplated. In addition, the cross-section shape may also be hexagonal or other suitable multi-lateral shape. The embodiments are not limited in this context.

Figure 2:
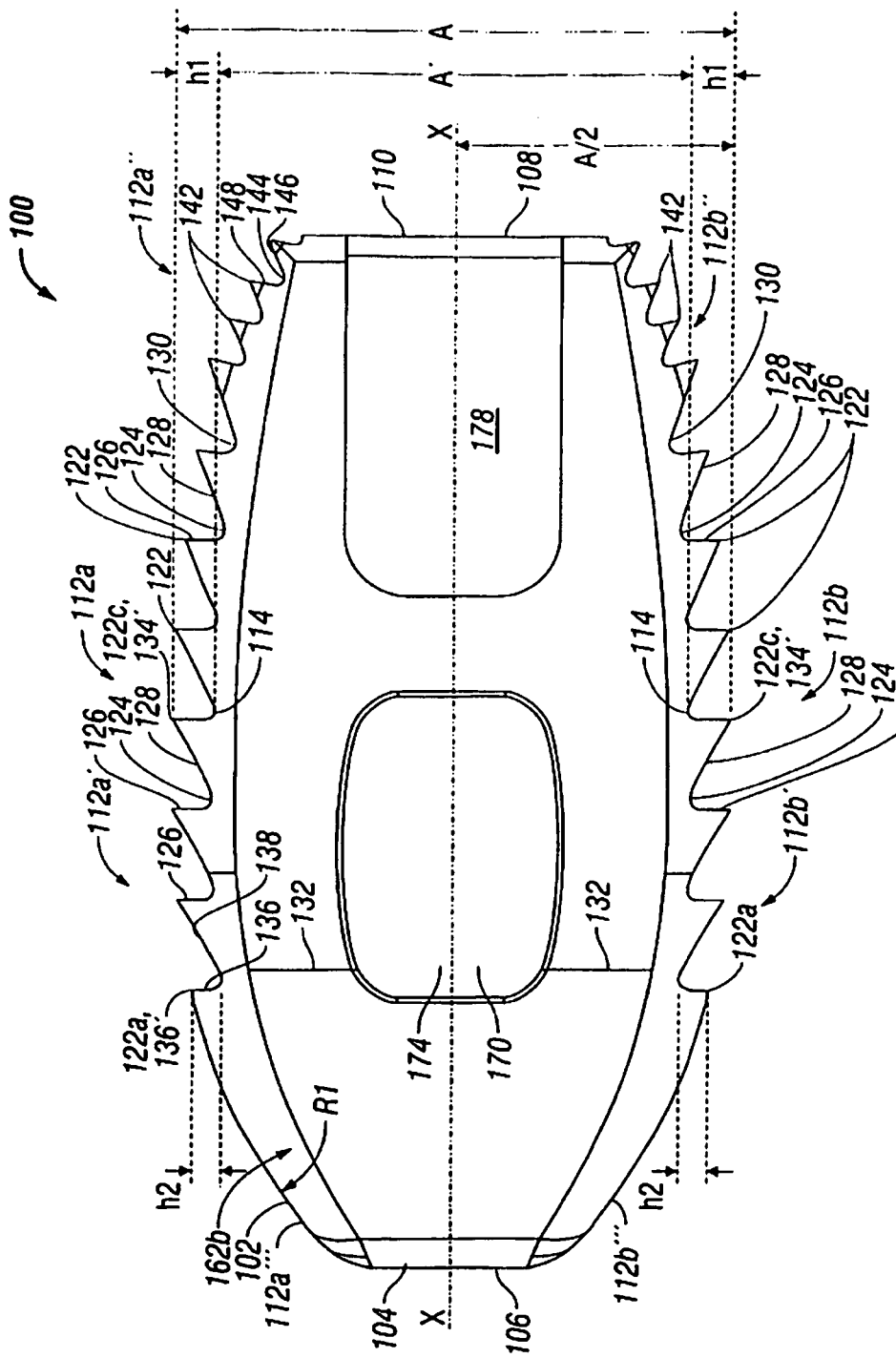
FIG. 2 is a side elevation view of the spinal interbody spacer of FIG. 1.
Figure 7:
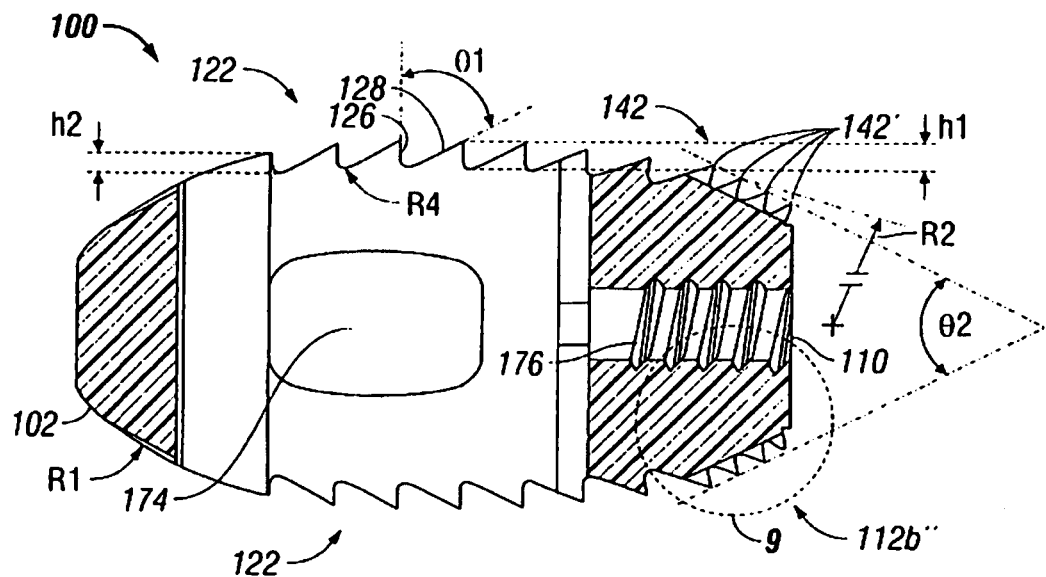
FIG. 7 is a side cross-sectional view of the spinal interbody spacer taken along cross-section line 7-7 of FIG. 6.

As best illustrated in FIGS. 2, 6, and 7, the body 102 is also configured such that the top and bottom vertebral engaging surfaces 112a, 112b, respectively, have a substantially streamlined convex profile, and are configured to be substantially symmetrical around a centerline axis X-X that extends from the distal end 106 to the proximal end 110. As best illustrated in FIGS. 3 and 4, the body 102 is configured such that the side surfaces 162a, 162b, respectively, have a substantially atraumatic blunt nose profile with respect to the contoured first end surface 104 and the substantially flat or planar second end surface 108. The intersection of the top and bottom surfaces 112a, 112b of the nose portion with the side surfaces 162a, 162b of the nose may be rounded to enhance the atraumatic character of the nose.

Figure 8:
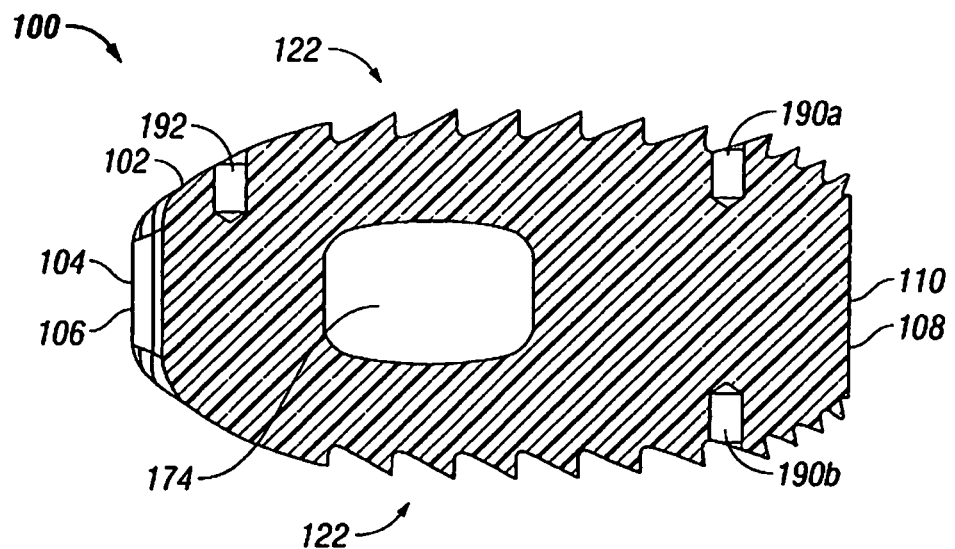
FIG. 8 is a side cross-sectional view of the spinal interbody spacer taken along section line 8-8 of FIG. 3 and FIG. 4.

FIG. 3 illustrates a plan view of the top vertebral engaging surface 112a while FIG. 4 illustrates a plan view of the bottom vertebral engaging surface 112b. As illustrated in FIGS. 3 and 4 by way of example, both surfaces 112a, 112b include at least first and second surface regions 112a', 112a" and 112b', 112b", respectively, that have distinct surface characteristics. As shown, surface regions 112a', 112b' are disposed distal to surface regions 112a", 112b". Referring to FIGS. 7-8, the surface characteristic of the first surface regions 112a', 112b' is such that the first surface regions 112a', 112b' (FIGS. 3 and 4) each have a plurality of protrusions 122 having a particular configuration. Similarly, the surface characteristic of the second surface regions 112a", 112b" is such that the second surface regions 112a", 112b" each have a plurality of protrusions 142 having a particular configuration. The configuration of the plurality of protrusions 142 of the second surface regions 112a", 112b" differs from the configuration of the plurality of protrusions 122 of the first surface regions 112a', 112b". The configuration of the plurality of protrusions 122 of the first surface regions 112a', 112b' is such that the plurality of protrusions 122 of the first surface regions 112a', 112b' define a first set of grooves 124 that face towards the second surface region. Each groove of the first set of grooves 124 has a position along the first surface regions 112a', 112b' of the top and bottom vertebral engaging surfaces 112a, 112b. Each groove of the first set of grooves 124 includes a first face 126 that is substantially orthogonal to the top and bottom vertebral engaging surfaces 112a, 112b, respectively, i.e., to the axis X, at the respective position of the groove. Each groove of the first set of grooves 124 includes a second opposing face 128. The second face 128 is substantially sloped or inclined with respect to the top and bottom vertebral engaging surfaces 112a, 112b, respectively, so that the surfaces 126, 128 converge at the bottom of the groove. The surfaces 126, 128 may directly intersect as shown or a further surface feature, such as a flat surface portion substantially parallel to axis X-X (see FIG. 2) may extend between and connect surfaces 126, 128.

Referring again to FIGS. 2-6, the first and second surface regions 112a', 112b' and 112a", 112b", respectively, may be contiguous surface regions forming a border 130 therebetween. The top and bottom vertebral engaging surfaces 112a, 112b, respectively, may also include third surface regions 112a''', 112b''' that extend from the substantially contoured first end surface 104 toward a distal edge 132 of the first surface regions 112a', 112b'. The third surface regions 112a''', 112b''' have surface characteristics that are distinct from the surface characteristics of the first surface regions 112a', 112b', and distinct from the surface characteristics of the second surface regions 112a", 112b". The first surface regions 112a', 112b' may extend from the distal edge 132 toward the border 130 with the second surface region 112a", 112b". The second surface regions 112a", 112b" may extend from the border 130 to the second end surface 108. The third surface regions 112a''', 112b''' are contiguous to the first surface regions 112a', 112b'. In the exemplary embodiment illustrated in FIGS. 1-12, the third surface regions 112a''', 112b''' are illustrated as being distal of and contiguous to the first surface regions 112a', 112b' The first set of grooves 124 defined by the plurality of protrusions 122 of the first surface regions 112a', 112b' face towards the second surface regions, 112a", 112b".

In this embodiment, the plurality of protrusions 122 of the first surface regions 112a', 112b' may further define a second set of grooves or channels 134 that exist along a longitudinal axis of the body 102. Each channel or groove of the second set of grooves 134 includes a first face 136 and a second opposing face 138. The first face 136 and the second face 138 of the grooves 134 may directly intersect as shown or a further surface feature, such as a flat surface portion may extend between and connect these surfaces:

The configuration of the plurality of protrusions 142 of the second surface regions 112a", 112b" is such that the plurality of protrusions 142 of the second surface regions 112a", 112b" define a set of substantially pyramidal protrusions. Each of the plurality of pyramidal protrusions 142 has a position along the third and fourth surface regions of the top and bottom vertebral engaging surfaces 112a, 112b. Each of the plurality of pyramidal protrusions 142 defines a first sloped face 146 (FIGS. 3 and 9) facing towards the distal end 104 of the body 102. In addition, each of the plurality of pyramidal protrusions 142 defines a second face 148 facing towards proximal end 110.

Figure 12:
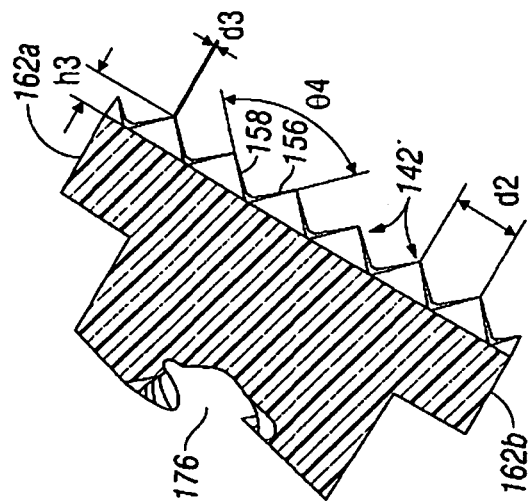
FIG. 12 is a partial cross-sectional view of the spinal interbody spacer taken along section line 12-12 of FIG. 11.
Figure 11:
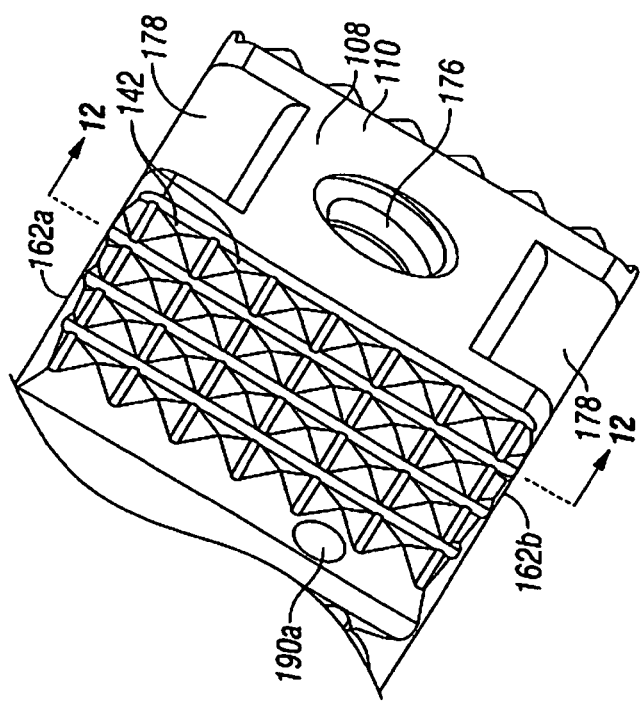
FIG. 11 is a partial perspective view of a surface region and trailing or proximal end of the spinal interbody spacer.

As shown in FIGS. 3, 4 and 12, each of the plurality of semi-pyramidal protrusions 142 defines a third sloped face 156 facing towards one side surface 162a and a fourth sloped face 158 facing towards the other side surface 162b. At least one of the third sloped faces 156 and at least one of the fourth sloped faces 158 defines a groove or flat space 154 between each pyramidal protrusion.

Referring to FIGS. 2 and 7, it can be seen that body 102 has a baseline height dimension A' as measured by the distance between base 114 of third protrusion 122c on the top vertebral engaging surface 112a and the base 114 of third protrusion 122c on the bottom vertebral engaging surface 112b that may range from about 7 millimeters (mm) to about 17 mm. The body 102 has a maximum height dimension A as measured by the distance between tip 134' of third protrusion 112c on the top vertebral engaging surface 112a and the tip 134' of third protrusion 122c on the bottom vertebral engaging surface 112b that may range from about 8.6 millimeters (mm) to about 18.6 mm. Height h1 of the protrusions 122 as measured by the distance between the base 114 of the third protrusion 122c and the tip 134' of the third protrusion 122c may be about 0.8 mm.

First protrusion 122a of the plurality of protrusions 122 on the top and bottom vertebral engaging surfaces 112a, 112b, respectively, has a height h2 as measured by the distance between base 136 of the first protrusion 122a and tip 136' of the first protrusion 112a of about 0.6 mm. The tips 134' of the plurality of protrusions 122 on the top and bottom vertebral engaging surfaces 112a, 112b are configured to align with the convex streamline profile of the top and bottom vertebral engaging surfaces 112a, 112b, respectively, such that the tips 134' form a radius of curvature R2 that may be about 50.8 mm (FIG. 7). The first face 126 of the grooves of the first set of grooves 124 of the plurality of protrusions 122 and the second face 128 that is substantially sloped or inclined with respect to the top and bottom vertebral engaging surfaces 112a, 112b may define an angle θ1 of about 63.5 degrees (see FIG. 7). For manufacturing purposes, the intersection between the first face 126 and the second face 128 may define a radius of curvature R4 that may be about 0.25 mm. Alternatively, as described above, a further surface feature such as a flat surface portion between surfaces 126, 128 may be provided.

The plurality of semi-pyramidal protrusions 142 of the second surface regions 112a", 112b" each have a tip 142' (see FIGS. 7 and 9) such that the tips 142' are aligned with the second surface regions 112a", 112b" to form an angle θ2 (see FIG. 7) between the second surface region 112a" and the second surface region 112b" of about 50 degrees at the proximal end 108 of the substantially streamlined convex profile.

Figure 9:
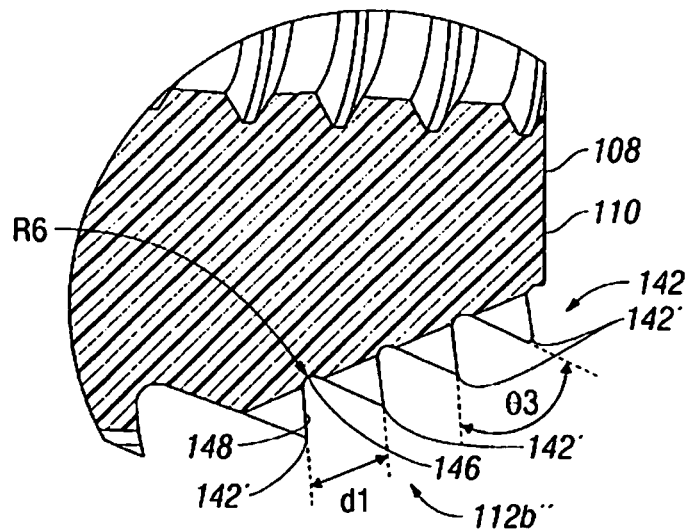
FIG. 9 is an enlarged view of the detail area 9 of FIG. 7.
Figure 10:
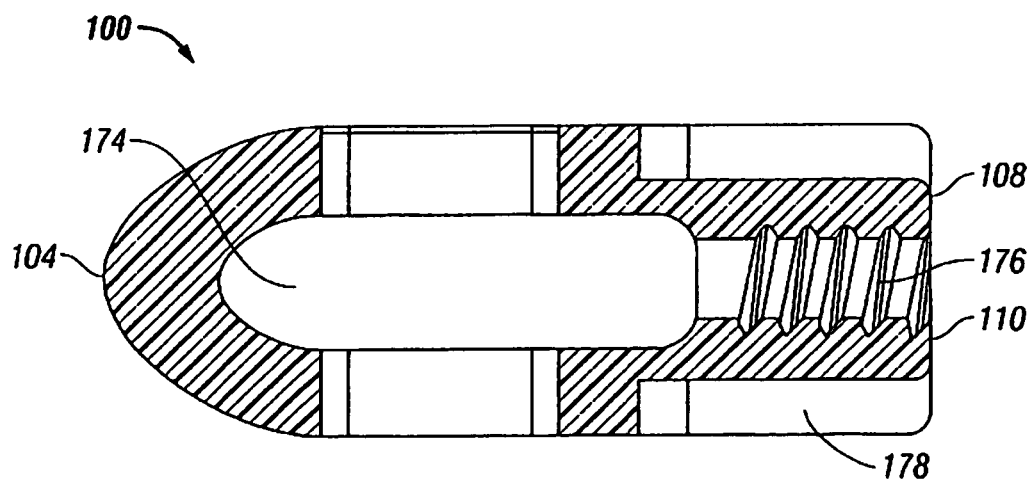
FIG. 10 is a top cross-sectional view of the spinal interbody spacer taken along section line 10-10 of FIG. 6.

Referring also to FIG. 9, the first sloped face 146 oriented towards the distal end 104 of the body 102 and the second face 148 oriented towards proximal end 108 and substantially orthogonal to the top and bottom vertebral engaging surfaces 112a, 112b form an angle θ3 that may be about 60 degrees. For manufacturing purposes, the groove 144 therebetween (FIG. 2) may have a radius of curvature R6 of about 0.13 mm. The pitch between the second faces 148 is defined by a distance d1 that may be about 0.9 mm. Alternatively, it is contemplated that the angle θ3 between the first sloped face 146 and the second sloped face 148 may be about 90 degrees.

Referring to FIG. 12, the third sloped face 156 facing towards side surface 162a and the fourth sloped face 158 facing towards the other side surface 162b define an angle θ4 that may be about 84 degrees. The pitch between the tips 142' in the direction transverse to the side surfaces 162a, 162b is defined by a distance d2 that may be about 1.2 mm. The tips 142' have a "flat-head" distance d3 between the third sloped face 156 and the fourth sloped face 158 of about 0.076 mm. Specifically, each tip 142' terminates in an apex having a planar surface that has a length dimension defined as d3.

Additionally, the third surface regions 112a''', 112b''' of surfaces 112a, 112b, respectively (see FIG. 2) are configured to align with the convex streamline profile of the top and bottom vertebral engaging surfaces 112a, 112b, respectively, such that the third surface regions 112a''', 112b''' define a radius of curvature R1 of about 13 mm, and more specifically about 13.33 mm, thereby forming rounded surfaces (see FIG. 2).

Referring to FIGS. 3-6, as previously discussed with respect to FIGS. 3 and 4, the body 102 is configured such that each of the side surfaces 162a, 162b, respectively, has a substantially atraumatic blunt nose profile with respect to the contoured first end surface 104 and the substantially flat second end surface 108. More particularly, to form the atraumatic blunt nose profile, the set of side surfaces 162a, 162b may further include contoured distal surface regions 162a', 162b' that extend from the contoured first end surface 104 at the distal end to transition regions 164a, 164b where the set of side surfaces 162a, 162b, respectively, transition to substantially flat side surfaces. The contoured distal surface regions 162a', 162b' may form a radius of curvature R5 that may be about 7.6 mm. Alternatively, it is contemplated that distal surface regions 162a', 162b' may be substantially planar surfaces, with rounded corners transitioning from the planar surfaces to the flat sides of the body and to the third surface regions 112a''', 112b'''. The body 102 has a length dimension L1 extending from the contoured first end surface 104 at the distal end to the second end surface 108 at the proximal end 110 that may be about 22 mm. The body 102 has a width dimension B as defined by the distance between side surface 162a and side surface 162b that may be about 8.5 mm. The contoured distal surface regions 162a', 162b' define the radius of curvature R5 and the third surface regions 112a''', 112b''' define the radius of curvature R1 and converge to form the substantially contoured first end surface or rounded shape 104 between the top and bottom surfaces 112a, 112b, respectively, As previously discussed with respect to FIGS. 5 and 6, the body 102 is configured such that the top and bottom vertebral engaging surfaces 112a, 112b intersect with the third and fourth surfaces 162a, 162b, respectively, to provide a substantially quadrilateral cross-section with rounded corners 140. The rounded corners 140 form a radius of curvature R3 that may be about 1.27 mm.

Referring again to FIGS. 1 and 2, the body 102 may further include an aperture 170 formed therein that extends transversely across the body 102 through the side surfaces 162a, 162b. The aperture 170 may be disposed transversely under at least a portion of the first surface region 112a' and over at least a portion of the first surface region 112b'.

Referring again to FIGS. 1 and 3, the body 102 may further include an aperture 172 formed therein that may extend vertically through the body 102.

The paths of the apertures 170, 172 intersect to form a hollow central region 174 of the body 102. The apertures 170, 172 and the hollow central region 174 may be filled with osteoconductive or osteoinductive materials (e.g. bone, bone chips, bone substitutes, bone growth promoting materials such as bone morphogenic proteins, etc.), or both, to enable and/or promote growth of vertebral bone therebetween to anchor the spinal interbody spacer 100 within the spine of a patient.

Referring again to FIGS. 3 and 4, as discussed above, the plurality of protrusions 122 of the first surface regions 112a', 112b' may further define the second set of grooves or channels 134 oriented towards the distal end 106 of the body 102. The aperture 172 forming the central hollow region 174 may be disposed within the body 102 to form a first lateral edge 172' substantially parallel to side surface 162a and a second lateral edge 172" substantially parallel to the fourth surface 162b such that a first line 184' of the second set of grooves or channels 134 are disposed between the first lateral edge 172' and the side 162a and a second line 184" of the second set of grooves or channels 134 are disposed between the second lateral edge 172" and the side 162b. The first line 184' and the second line 184" are disposed symmetrically with respect to the centerline axis X-X that extends from the distal end to the proximal end 110. A third line 184'" of the second set of grooves or channels 134 may be disposed along the centerline axis X-X to bisect the third surface region 112a", 112b' and also along at least the most proximal of the plurality of protrusions 122.

As best shown in FIGS. 3 and 8, the top vertebral engaging surface 112a differs from the bottom vertebral engaging surface 112b in that the top vertebral engaging surface 112a includes at least one aperture 190a formed therein and at least partially penetrating therethrough, and at least one second aperture 192 formed therein and at least partially penetrating therethrough. In contrast, as best shown in FIGS. 4 and 8, the bottom vertebral engaging surface 112b includes at least one aperture 190b formed therein and at least partially penetrating therethrough, but not necessarily another aperture. The apertures 190a, 190b and 192 are configured to receive an optional fiduciary insert (not shown), thus allowing the orientation of the spinal interbody spacer 100 to be determined using a number of different imaging modalities as are known in the art. This feature is particularly important when spacer 100 is made from a substantially radiolucent material (e.g. polyetheretherketone or PEEK).

Referring to FIGS. 1, 2, 6, 7, 10, 11 and 12, the proximal end 110 of the body 102 may further include an internally threaded aperture 176 disposed through the second end surface 108 communicating with the hollow central region 174. The internally threaded aperture 176 enables engagement with a corresponding threaded end of an insertion tool (not shown). The body 102 may also be configured such that a set of depressions 178 are formed therein at the proximal end 110 of the body 102 in a manner to be symmetrically disposed adjacent to the aperture 176 and to provide a substantially I-shaped configuration to the second end surface 108 at the proximal end 110. The depressions 178 are further configured to enable engagement with stabilizing jaws of a spacer insertion device to facilitate the insertion of the spinal interbody spacer 100.

Referring now to FIGS. 13-21, another embodiment of a spinal interbody spacer is disclosed and has a number of features in common with the spinal interbody spacer 100 described above. For that reason, except for the specific differences described below, analogous features are designated by a 200 series nomenclature that correspond to the previously discussed 100 series designation. More particularly, referring to FIGS. 13-16, in this embodiment, spinal interbody spacer 200 includes a body 202 having a substantially contoured first end surface 204 at a distal or leading end 206 of the body 202 and a second end surface 208 opposite thereto at a proximal or trailing end 210 of the body 202. The body 202 extends between the first and second end surfaces, 204, 208, respectively, to define top and bottom vertebral engaging surfaces 212a, 212b, respectively. The top and bottom vertebral engaging surfaces 212a, 212b, respectively, are disposed opposite to one another. The body 202 also extends between the first and second end surfaces, 204, 208, respectively, to define opposing side surfaces 262a, 262b, respectively.

Figure 13:
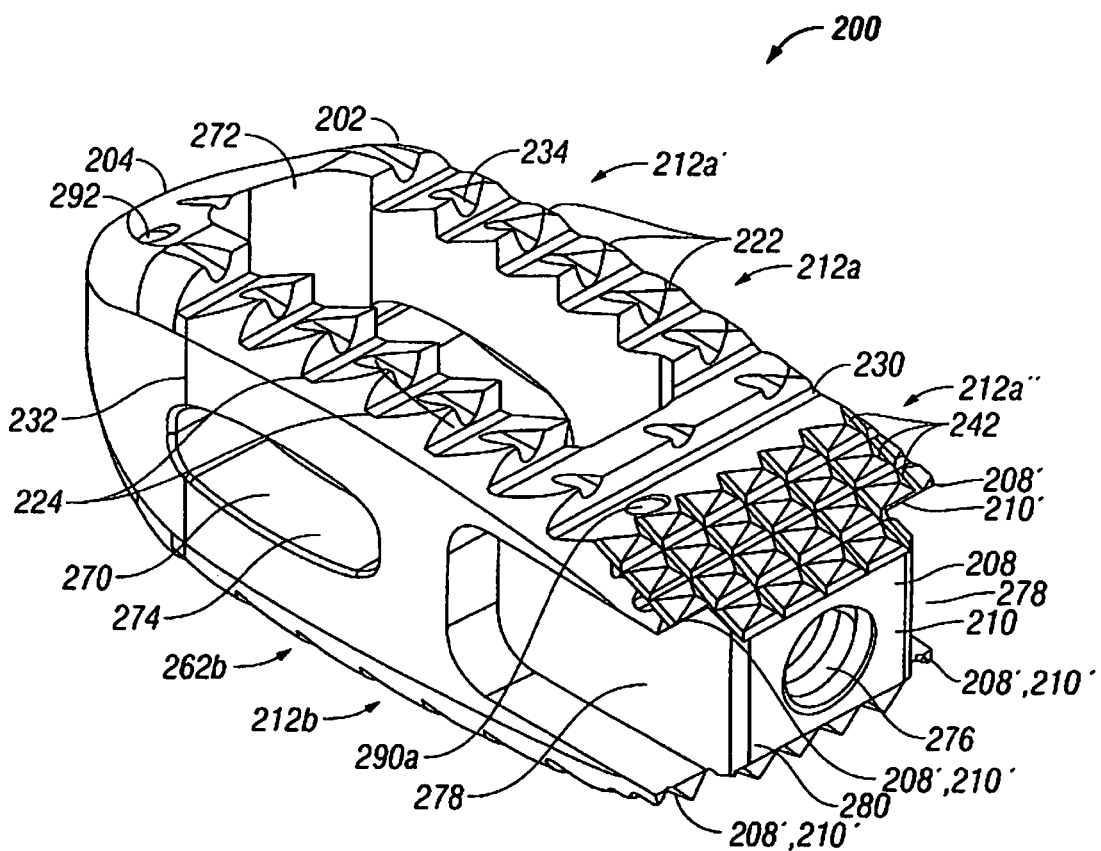
FIG. 13 is a perspective view generally from a trailing or proximal end of another embodiment of a spinal interbody spacer according to the present disclosure.
Figure 14:
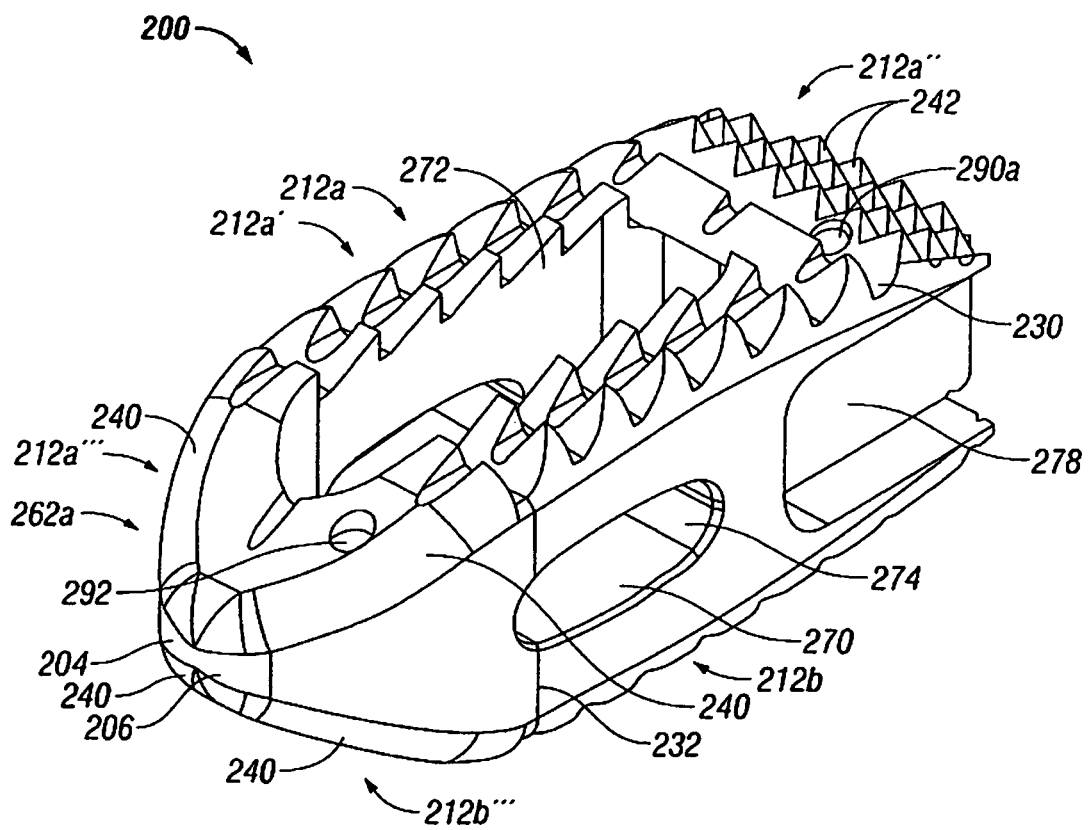
FIG. 14 is a perspective view generally from a leading end of the embodiment of a spinal interbody spacer of FIG. 13.
Figure 16:
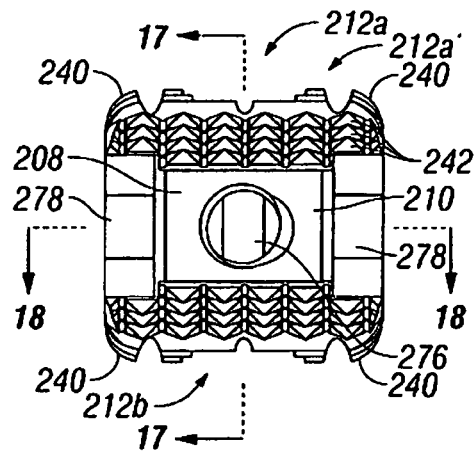
FIG. 16 is a rear elevational view of the trailing end of the spinal interbody spacer; of FIGS. 13 and 14.

As best illustrated in FIGS. 13, 14 and 16, the body 202 is configured such that the top and bottom vertebral engaging surfaces 212a, 212b intersect the side surfaces 262a, 262b, respectively, to provide a substantially quadrilateral cross-section with rounded corners 240. As illustrated in FIG. 16, the body 202 has, by way of example, a substantially rectangular cross-section, although other quadrilateral shapes such as a square are also contemplated. In addition, the cross-section shape may also be hexagonal or other suitable multilateral shape. The embodiments are not limited in this context.

As best illustrated in FIGS. 13-15, 17 and 21, the body 202 is also configured such that the top and bottom vertebral engaging surfaces 212a, 212b, respectively, have a substantially planar profile and are configured to be substantially symmetrical around a centerline axis X'-X' that extends from the distal end 206 to the proximal end 210.

Figure 19:
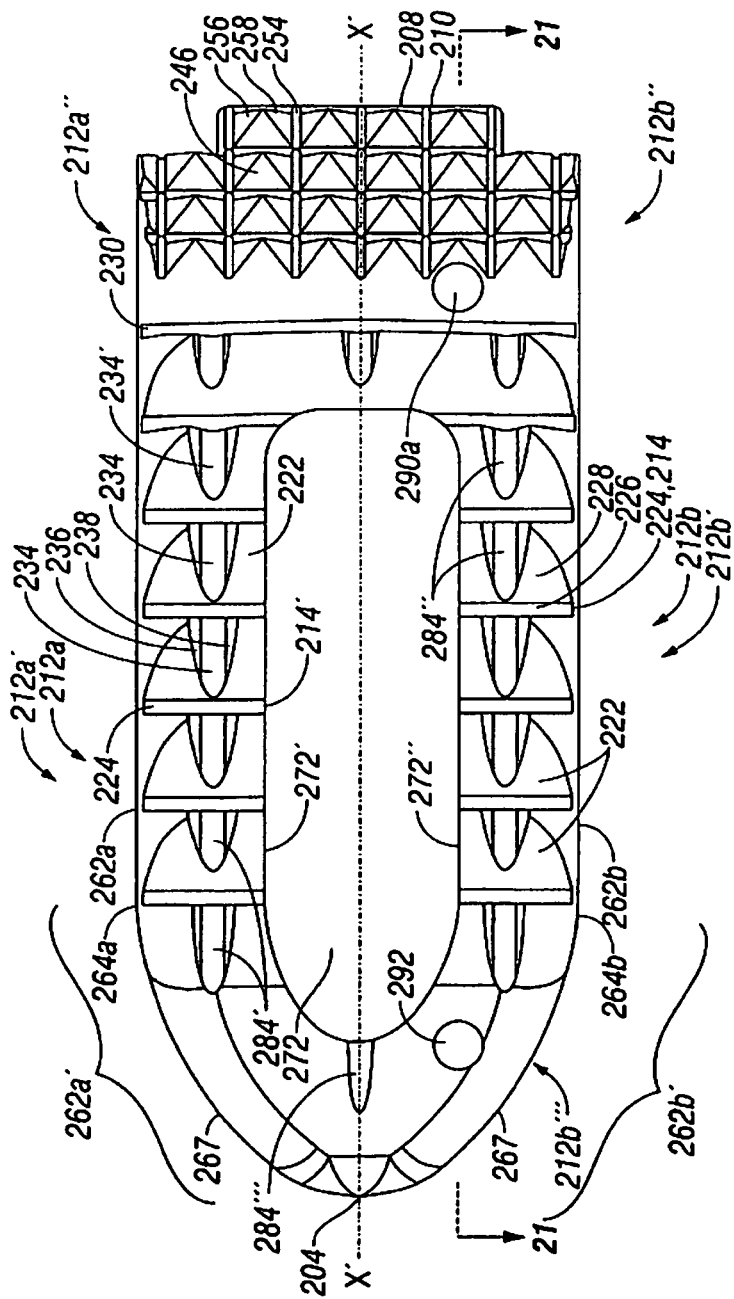
FIG. 19 is top plan view of the spinal interbody spacer of FIGS. 13 and 14 showing a vertebral-engaging surface.
Figure 20:
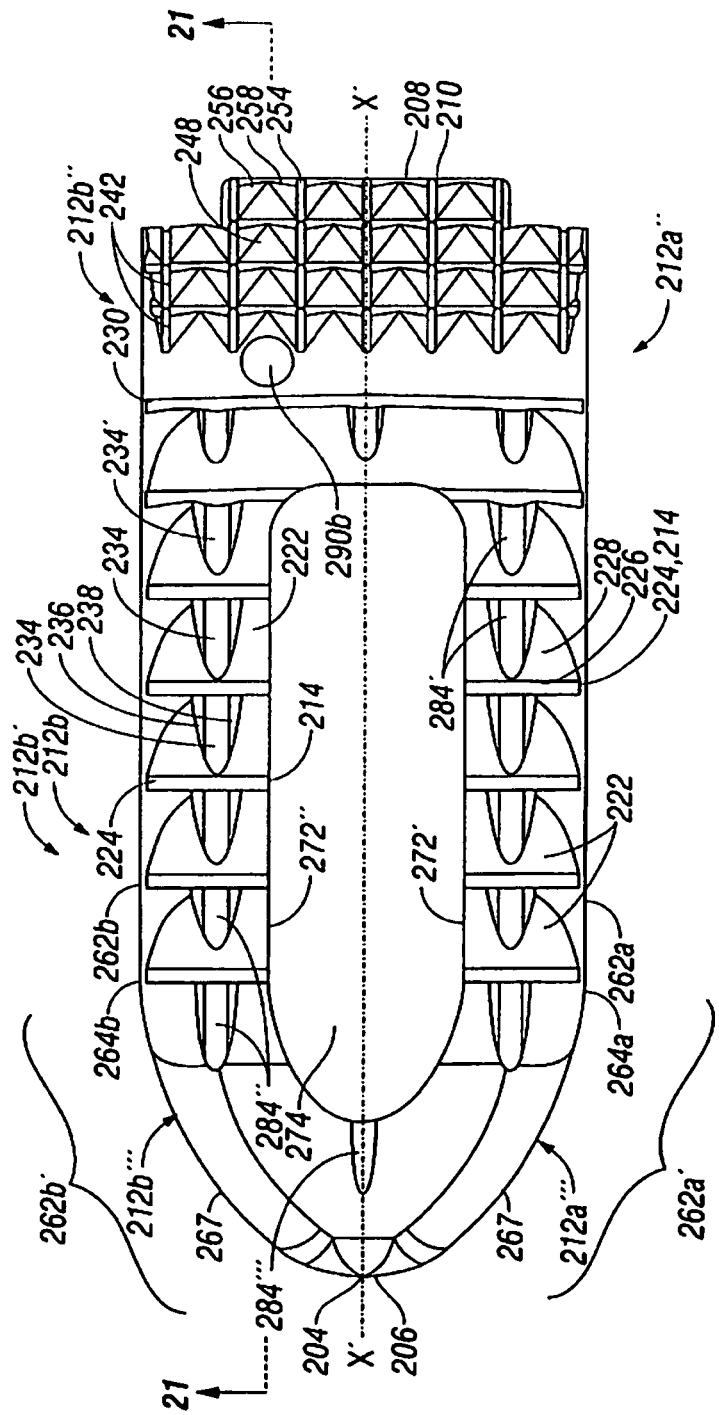
FIG. 20 is a bottom plan view of the spinal interbody spacer of FIGS. 13 and 14 showing another vertebral-engaging surface.

As best illustrated in FIGS. 19 and 20, the body 202 is configured such that the top and bottom surfaces 212a, 212b, respectively, have a substantially atraumatic blunt nose profile with respect to the contoured first end surface 204 and the substantially flat or planar second end surface 208. That is, the body 202 is configured such that the substantially planar or flat top and bottom surfaces 212a, 121b, respectively. and the convex side surfaces 262a, 262b, respectively, converge at the distal end 206 of the body 202 to define a substantially atraumatic blunt nose having a tip 205 configured at least partially with planar surfaces 207 defined by the top and bottom surfaces 212a, 212b, respectively, and rounded surfaces 267 defined by the side surfaces 262a, 262b, respectively.

Figure 15:
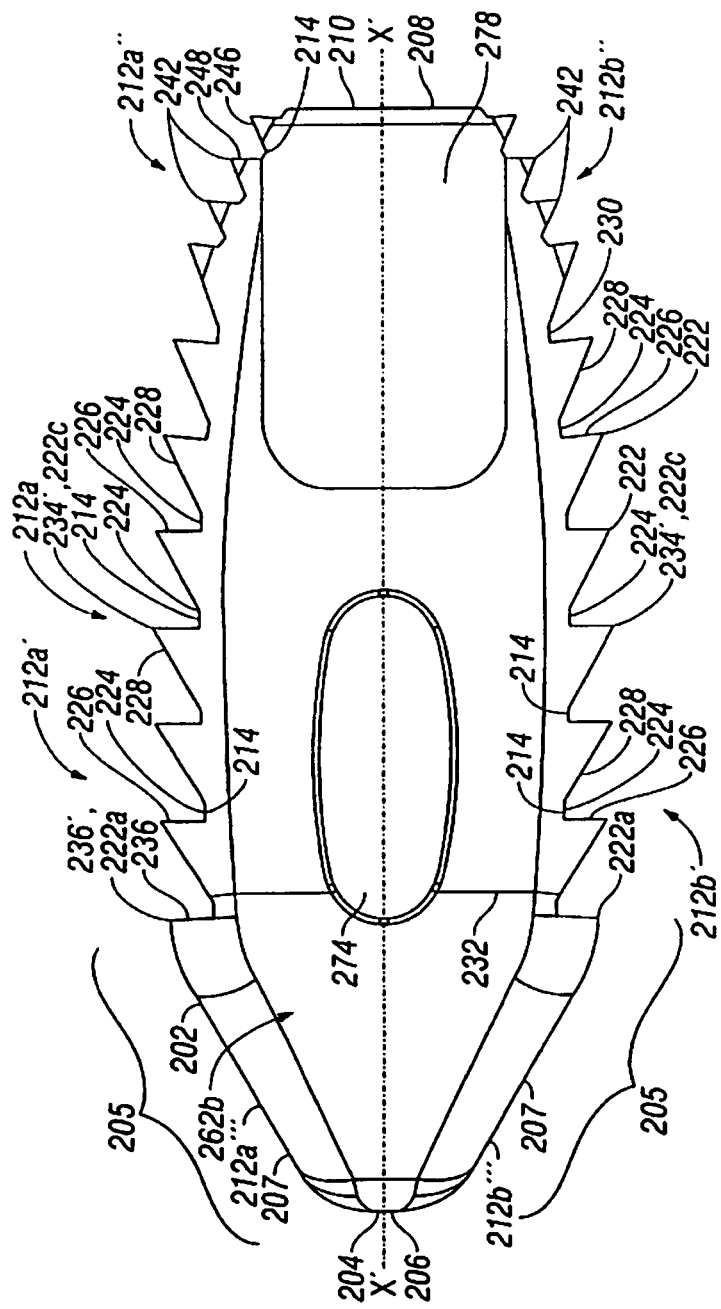
FIG. 15 is a side elevational view of the spinal interbody spacer of FIGS. 13 and 14.
Figure 17:
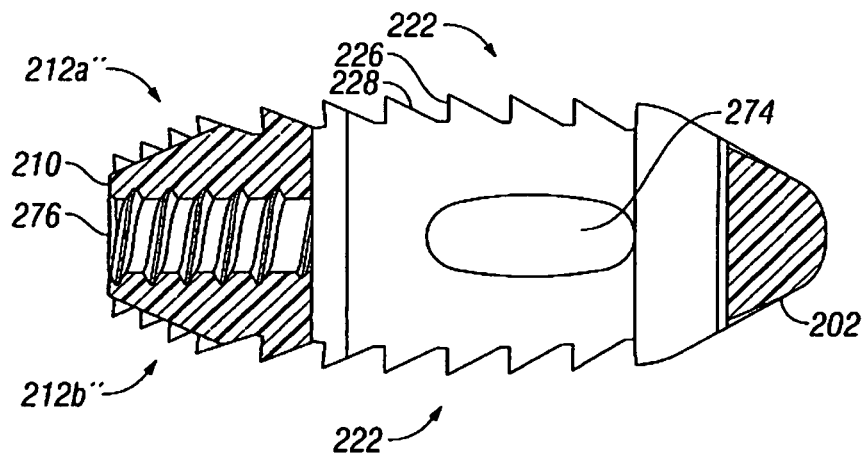
FIG. 17 is a side cross-sectional view of the spinal interbody spacer taken along cross-section line 17-17 of FIG. 16.
Figure 18:
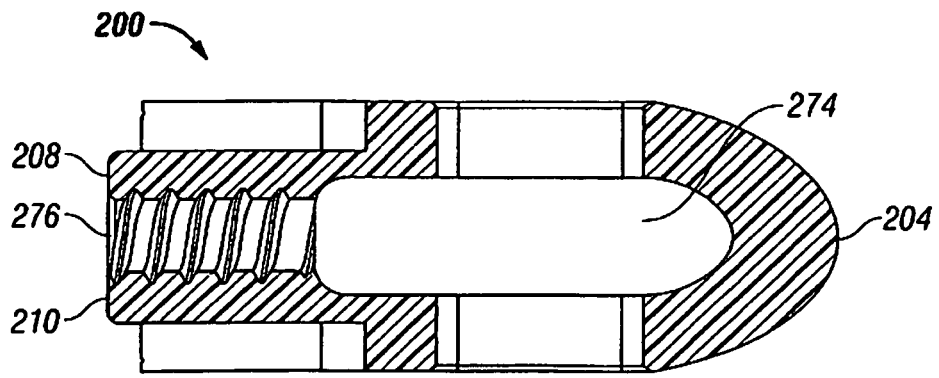
FIG. 18 is a top cross-sectional view of the spinal interbody spacer taken along section line 18-18 of FIG. 16.
Figure 21:
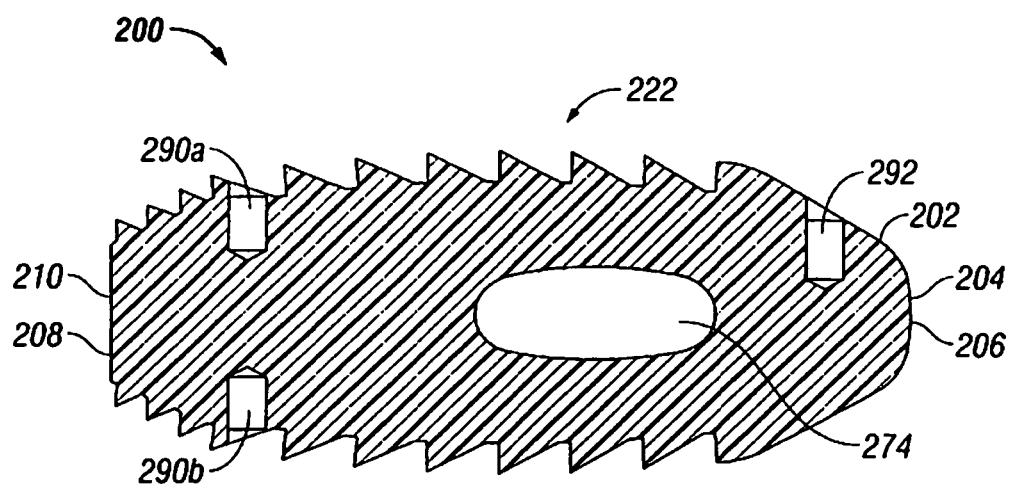
FIG. 21 is a side cross-sectional view of the spinal interbody spacer taken along cross-section line 21-21 of FIGS. 19 and 20.

FIG. 19 illustrates a plan view of the top vertebral engaging surface 212a while FIG. 20 illustrates a plan view of the bottom vertebral engaging surface 212b. As illustrated in FIGS. 19 and 20 by way of example, both surfaces 212a, 212b include at least first and second surface regions 212a', 212a" and 212b', 212b", respectively, that have distinct surface characteristics. Referring also to FIGS. 15, 17 and 21, the surface characteristic of the first surface regions 212a', 212b' is such that the first surface regions 212a', 212b' each have a plurality of protrusions 222 having a particular configuration. Similarly, the surface characteristic of the second surface regions 212a", 212b" is such that the second surface regions 212a", 212b'' each have a plurality of protrusions 242 having a particular configuration. The configuration of the plurality of protrusions 242 of the second surface regions 212a'', 212b'' differs from the configuration of the plurality of protrusions 222 of the first surface regions 212a', 212b'. The configuration of the plurality of protrusions 222 of the first surface regions 212a', 212b' is such that the plurality of protrusions 222 of the first surface regions 212a', 212b' define a first set of grooves 224. Each groove of the first set of grooves 224 has a position along the first surface regions 212a', 212b' of the top and bottom vertebral engaging surfaces 212a, 212b. Each groove of the first set of grooves 224 includes a first face 226 that is substantially orthogonal to the top and bottom vertebral engaging surfaces 212a, 212b, respectively, i.e., to the axis X'-X', at the respective position of the groove. Each groove of the first set of grooves 224 includes a second opposing face 228. The second face 228 is substantially sloped or inclined with respect to the top and bottom vertebral engaging surfaces 212a, 212b, respectively, so that the surfaces or faces 226, 228 converge at the bottom of the groove. The surfaces 226,228 may intersect via a flat surface portion 214 that may be substantially parallel to axis X'-X' (see FIG. 15) and that may extend between and connect surfaces or faces 226, 228. The faces or surfaces 226 and the flat surface portions 214 intersect to define an orthogonal angle at their junction. Thus, at least a portion of a bone engaging region between the first face 226 and second face 228 is configured as a flat surface 214.

Referring again to FIG. 13-15, the first and second surface regions 212a, 212b' and 212a'', 212b'', respectively, may be contiguous surface regions forming a border 230 therebetween. The top and bottom vertebral engaging surfaces 212a, 212b, respectively, may also include third surface regions 212a''', 212b''' that extend from the substantially contoured first end surface 204 toward a distal edge 232 of the first surface regions 212a', 212b'. The third surface regions 212a''', 212b''' have surface characteristics that are distinct from the surface characteristics of the first surface regions 212a', 212b', and distinct from the surface characteristics of the second surface regions 212a'', 212b''. The first surface regions 212a', 212b' may extend from the distal edge 232 toward the border 230 with the second surface region 212a'', 212b''. The second surface regions 212a'', 212b' may extend from the border 230 to the second end surface 208. The third surface regions 212a''', 212b''', are contiguous to the first surface regions 212a', 212b' and extend to the distal tip of the spacer 200. In the exemplary embodiment illustrated in FIGS. 13-21, the third surface regions 212a''', 212b''' are illustrated as being distal of and contiguous to the first surface regions 212a, 212b' The first set of grooves 224 defined by the plurality of protrusions 222 of the first surface regions 212a', 212b' face towards the second and third surface regions, 212a'', 212b'' and 212a''', 212b''', respectively.

Referring to FIGS. 19-20, the plurality of protrusions 222 of the first surface regions 212a', 212b' may further define a second set of grooves or channels 234 that exist along a longitudinal axis of the body 202. Each channel or groove of the second set of grooves 234 includes a first face 236 and a second opposing face 238. The first face 236 and the second face 238 of the grooves 234 may directly intersect as shown or a further surface feature, such as a flat surface portion 234' may extend between and connect these surfaces.

The configuration of the plurality of protrusions 242 of the second surface regions 212a'', 212b'' is such that they define a set of substantially pyramidal protrusions. Each of the plurality of pyramidal protrusions 242 has a position along the third and fourth surface regions of the top and bottom vertebral engaging surfaces 212a, 212b. Each of the plurality of pyramidal protrusions 242 defines a first sloped face 246 facing towards the distal end 204 of the body 202. In addition, each of the plurality of pyramidal protrusions 242 defines a second face 248 facing towards the proximal end 208 surface of the body 202 and substantially orthogonal to the top and bottom vertebral engaging surfaces 212a, 212b at the respective position of the pyramidal protrusion 242. The first and second faces 246, 248 respectively may directly intersect or a further surface feature such as a flat surface portion 244 may extend between and connect faces 246, 248.

Each of the plurality of semi-pyramidal protrusions 242 defines a third sloped face 256 facing towards the third surface 262a and defines a fourth sloped face 258 facing towards the fourth surface 262b. At least one of the third sloped faces 256 and at least one of the fourth sloped faces 258 defines a groove or flat space 254 between each pyramidal protrusion.

The body 202 is configured such that each of the side surfaces 262a, 262b, respectively, has a substantially atraumatic blunt nose profile with respect to the contoured first end surface 204 and the substantially flat second end surface 208. More particularly, to form the atraumatic blunt nose profile, the side surfaces 262a, 262b may further include contoured distal surface regions 262a', 262b' that extend from the contoured first end surface 204 at the distal end to transition regions 264a, 264b where the side surfaces 262a, 262b, respectively, transition to substantially flat surfaces. Alternatively, it is contemplated that distal surface regions 262a', 262b' may be substantially planar surfaces, with rounded corners 240 transitioning from the planar surfaces to the flat sides 262a, 262b of the body 202 and to the third surface regions 212a''', 212b'''. However, if side surfaces 262a', 262b' are substantially planar, the end surfaces 204 may be either planar or convex.

Referring again to FIGS. 13-15, in a similar manner as with respect to spinal interbody spacer 100 discussed above, the body 202 of spinal interbody spacer 200 may further include an aperture 270 formed therein that extends transversely across the body 202 through the side surfaces 262a, 262b. The aperture 270 may be disposed transversely under at least a portion of the first surface region 212a' and over at least a portion of the first surface region 212b'. The body 202 may further include an aperture 272 formed therein that may extend vertically through the body 202 through the first surface regions 212a', 212b' and third surface regions 212a''', 212b'''. The paths of the apertures 270, 272 intersect to form a hollow central region 274 of the body 202. The apertures 270, 272 and the hollow central region 274 enable growth of vertebral bone therebetween to anchor the spinal interbody spacer 200 within the spine of a patient. The hollow central region 274 may be filled with osteoconductive or osteoinductive materials (e.g. bone, bone chips, bone substitutes, bone growth promoting materials such as bone morphogenic proteins, etc.), or both, to enable and/or promote growth of vertebral bone therebetween to anchor the spinal interbody spacer 200 within the spine of a patient.

Referring again to FIGS. 19 and 20, as discussed above, the plurality of protrusions 222 of the first surface regions 212a', 212b' may further define the second set of grooves or channels 234 oriented towards the distal end 206 of the body 202. The aperture 272 forming the central hollow region 274 may be disposed within the body 202 to form a first lateral edge 272' substantially parallel to the side surface 262a and a second lateral edge 272'' substantially parallel to the side surface 262b such that a first line 284' of the second set of grooves or channels 234 are disposed between the first lateral edge 272' and side surface 262a and a second line 284'' of the second set of grooves or channels 234 are disposed between the second lateral edge 272" and side surface 262b. The first line 284' and the second line 284" are disposed symmetrically with respect to the centerline axis X'-X' that extends from the distal end 206 to the proximal end 210. A third line 284''' of the second set of grooves or channels 234 may be disposed along the centerline axis X'-X' to bisect the third surface region 212a''', 212b''' and also along at least the most proximal of the plurality of protrusions 222.

As best shown in FIGS. 19 and 21, the bottom vertebral engaging surface 212b differs from the top vertebral engaging surface 212a in that the top vertebral engaging surface 212a includes at least one aperture 290a formed therein and at least partially penetrating therethrough at least one aperture 292 formed therein and at least partially penetrating therethrough. In contrast, as best shown in FIGS. 20 and 21, the bottom vertebral engaging surface 212b includes within second surface region 212b" at least one aperture 290b formed therein and at least partially penetrating therethrough, but not necessarily another aperture formed within bottom vertebral engaging surface 212b. The apertures 290a, 290b and 292 are configured to receive an optional fiduciary insert (not shown), thus allowing the orientation of the spinal interbody spacer 200 to be determined using a number of different imaging modalities as are known in the art.

Referring to FIGS. 13 and 16-18, the body 202 includes at the trailing end 208 a central portion 280 between top and bottom vertebral engaging surfaces 212a, 212b, respectively. The central portion 280 extends from the proximal end 210. The central portion 280 may further include an internally threaded aperture 276 disposed through the second end surface 208 communicating with the hollow central region 274. The internally threaded aperture 276 enables engagement with a corresponding threaded end of an insertion tool (not shown). The central portion 280 is configured with a width that is less than the width of the body 202 such that a set of depressions 278 are formed therein at the proximal end 210 of the body 202 in a manner to be symmetrically disposed adjacent to the aperture 276 and to provide a substantially I-shaped configuration to the second end surface 208 at the proximal end 210. The depressions 278 are further configured to enable engagement with stabilizing jaws of a spacer insertion device to facilitate the insertion of the spinal interbody spacer 200.

In one embodiment, bordering portions of the second surface regions 212a", 212b" of spinal interbody spacer 200 include trailing ends 208' that extend only from proximal edges 210' that are distal with respect to the proximal end 210. The proximal edges 210' at the trailing ends 208' and the central portion 280 extending from the proximal end 210 form open corners 282 in proximity to the depressions 278.

Those skilled in the art will recognize that, and understand how, the dimensions identified previously in FIGS. 1-12 and discussed above, with respect to spinal interbody spacer 100 may be applied analogously to the spinal interbody spacer 200 illustrated in FIGS. 13-21.

Furthermore, it can be understood from the foregoing disclosure of the exemplary embodiments of spinal interbody spacers 100, 200 that the spacers 100, 200 provide spinal implants that provide a desired amount of lordosis, and a desired spacing between adjacent vertebral bodies, resist movement once inserted, and provide a path for bone ingrowth.

It will be understood that various modifications may be made to the embodiments of the presently disclosed spinal interbody spacer. Therefore, the above description should not be construed as limiting, but merely as exemplifications of embodiments. Those skilled in the art will envision other modifications within the scope and spirit of the present disclosure.

What is claimed is:

1. A spinal spacer for engagement between vertebrae, comprising:
a body defined along a longitudinal centerline axis and having a substantially contoured first end surface at a distal end of the body and a second end surface opposite thereto at a proximal end of the body,
the body extending between the first and second end surfaces to define top and bottom vertebral engaging surfaces, the top and bottom vertebral engaging surfaces disposed opposite to one another, the body further defining opposed side surfaces,
the body being configured such that the top and bottom vertebral engaging surfaces intersect with the side surfaces to provide a substantially quadrilateral cross-section with rounded corners,
the body being configured such that the top and bottom vertebral engaging surfaces have a substantially streamlined convex profile, and
the body being configured such that at least one of the top and bottom vertebral engaging surfaces further comprises a first, a second, and a third surface region, the first surface region disposed distally of the second surface region, the third surface region contiguous with the first surface region and aligned with the substantially streamlined convex profile so as to form rounded surfaces, each surface region having distinct surface characteristics, both the first and second surface regions having a plurality of protrusions with a configuration, each of the protrusions on the first surface region having a pair of walls with a groove therethrough, the plurality of protrusions of the first surface region further defining a set of channels extending along the body in the direction of the longitudinal centerline axis and being substantially symmetrical about the longitudinal axis,
the channels having a substantially semi-cylindrical cross-section,
each of the protrusions of the second surface region being substantially pyramidal and differing from the configuration of the plurality of protrusions of the first surface region
the second surface region disposed between the first surface region and the proximal end of the body;
wherein the first surface region is separated from the second surface region by a border, the border extending perpendicular to the longitudinal centerline axis, such that the border intersects the opposed side surfaces of the body;
wherein the top vertebral engaging surface includes a first aperture and a second aperture, the first and second apertures partially extending through the body, the first aperture disposed toward the first end surface of the body on the third surface region, and the second aperture disposed toward the second end surface of the body between the border and the plurality of protrusions of the second surface region;
wherein the bottom vertebral engaging surface includes a third aperture partially extending through the body, the third aperture disposed toward the second end surface of the body between the border and the second surface region; and
wherein the first and second apertures are aligned with respect to each other on the top vertebral engaging surface, and the second and third apertures are disposed in opposed relation to each other with respect to the longitudinal centerline axis.

2. The spinal spacer according to claim 1, wherein the substantially convex top and bottom surfaces and the side surfaces converge at the distal end of the body to define a substantially atraumatic blunt nose, the nose having a tip configured by a substantially planar surface defined by top and bottom surfaces and a rounded shape defined by the side surfaces.

3. The spinal spacer according to claim 1, wherein the plurality of protrusions of the second surface region define a set of pyramidal protrusions,
   each of the plurality of pyramidal protrusions having a position along the at least one of the first and second vertebral engaging surfaces having a substantially streamlined convex profile,
   each of the plurality of pyramidal protrusions defining a first sloped face oriented towards the distal end of the body,
   each of the plurality of pyramidal protrusions defining a second face substantially orthogonal to the at least one of the top and bottom vertebral engaging surfaces at the respective position of the pyramidal protrusion,
   the first sloped face and second face defining a bone engaging region therebetween.

4. The spinal spacer according to claim 3, wherein at least a portion of the bone engaging region extending between the first sloped face and second sloped face of the pyramidal protrusions is configured as a flat surface.

5. The spinal spacer according to claim 3, wherein
   each of the plurality of pyramidal protrusions defines a third sloped face oriented towards a third non-engaging surface, and
   each of the plurality of pyramidal protrusions defines a fourth sloped face oriented towards a fourth non-engaging surface, and wherein
   at least one of the third sloped faces and at least one of the fourth sloped faces defines a bone engaging region therebetween.

6. The spinal spacer according to claim 1, wherein
   the first and second surface regions are contiguous surface regions,
   the first surface region extending from the substantially contoured first end surface toward the border with the second surface region,
   the second surface region extending from the border to the second end surface.

7. The spinal spacer of claim 1, wherein at least one of the top and bottom vertebral engaging surfaces defines a radius of approximately 13 mm.

8. The spinal spacer of claim 1, further comprising a hollow inner body defined by at least one opening extending through the body.

9. The spinal spacer of claim 8, wherein the at least one opening extends through the top and bottom vertebral engaging surfaces.

10. The spinal spacer of claim 8, wherein the at least one opening extends through the side surfaces.

11. The spinal spacer of claim 8, wherein the at least one opening further comprises first and second intersecting openings, the first intersecting opening extending through top and bottom vertebral engaging surfaces, and the second intersecting opening extending through the side surfaces.

12. The spinal spacer of claim 1, further comprising a threaded tool engaging opening in the second end surface at the proximal end of the body.

13. The spinal spacer of claim 1, wherein each side further includes a depression adjacent the proximal end of the body.

14. The spinal spacer of claim 13, wherein the body at the depressions defines an I-beam cross-section.

15. The spinal spacer of claim 1, wherein the surface characteristics of the first region are different from the surface characteristics of the third region.

16. The spinal spacer of claim 15, wherein the surface characteristics of the second region are different from the surface characteristics of the first and third regions.

17. The spinal spacer of claim 1, wherein the grooves of the first surface region are substantially aligned defining the set of channels.

18. The spinal spacer of claim 1, wherein the first, second, and third apertures are configured to receive a fiduciary insert for allowing orientation of the spinal spacer to be determined by using different imaging modalities.

\* \* \* \* \*